United States Patent
Zhong et al.

(10) Patent No.: US 10,636,146 B2
(45) Date of Patent: Apr. 28, 2020

(54) MEDICAL IMAGE PROCESSING METHODS AND SYSTEMS

(71) Applicant: Singapore Health Services Pte Ltd, Singapore (SG)

(72) Inventors: Liang Zhong, Singapore (SG); Jun Mei Zhang, Singapore (SG); Ru San Tan, Singapore (SG)

(73) Assignee: Singapore Health Services Pte Ltd, Singapore (SG)

( * ) Notice: Subject to any disclaimer, the term of this patent is extended or adjusted under 35 U.S.C. 154(b) by 170 days.

(21) Appl. No.: 15/573,366

(22) PCT Filed: May 6, 2016

(86) PCT No.: PCT/SG2016/050213
§ 371 (c)(1),
(2) Date: Nov. 10, 2017

(87) PCT Pub. No.: WO2016/182508
PCT Pub. Date: Nov. 17, 2016

(65) Prior Publication Data
US 2018/0089829 A1    Mar. 29, 2018

(30) Foreign Application Priority Data

May 12, 2015    (SG) .......................... 10201503747W

(51) Int. Cl.
*G06K 9/00*    (2006.01)
*G06T 7/00*    (2017.01)
(Continued)

(52) U.S. Cl.
CPC ............ *G06T 7/0016* (2013.01); *A61B 6/032* (2013.01); *A61B 6/504* (2013.01); *A61B 6/507* (2013.01);
(Continued)

(58) Field of Classification Search
None
See application file for complete search history.

(56) References Cited

U.S. PATENT DOCUMENTS

2013/0246034 A1    9/2013 Sharma et al.
2014/0073976 A1    3/2014 Fonte et al.
(Continued)

FOREIGN PATENT DOCUMENTS

CN    103932694 A    7/2014
WO    2013/071219 A1    5/2013
(Continued)

OTHER PUBLICATIONS

Huo et al., A validated predictive model of coronary fractional flow reserve. J R Soc Interface. Jun. 7, 2012;9(71):1325-38.
(Continued)

*Primary Examiner* — Shervin K Nakhjavan
(74) *Attorney, Agent, or Firm* — McCarter & English, LLP; David R. Burns

(57) ABSTRACT

A medical image processing method of determining a fractional flow reserve through a stenosis of a coronary artery from medical image data is disclosed. The medical image data comprises a set of images of a coronary region of a patient. The coronary region includes the stenosis. The method comprises: reconstructing a three dimensional model of a coronary artery tree of the patient from the medical image data; determining stenosis dimensions from the three dimensional model of the coronary artery tree of the patient; simulating blood flow in the three dimensional model of the coronary artery tree of the patient to determine modeled flow rates; using an analytical model depending on the stenosis dimensions to predict a modeled pressure drop
(Continued)

over the stenosis from the modeled flow rates; and determining the fractional flow reserve through the stenosis from the modeled pressure drop.

23 Claims, 7 Drawing Sheets

(51) Int. Cl.
```
G06F 19/00      (2018.01)
A61B 6/03       (2006.01)
A61B 6/00       (2006.01)
G16H 50/50      (2018.01)
G06T 19/20      (2011.01)
G06T 7/60       (2017.01)
G06T 11/00      (2006.01)
```
(52) U.S. Cl.
CPC ............ *A61B 6/5217* (2013.01); *G06F 19/00* (2013.01); *G06F 19/321* (2013.01); *G06T 7/0012* (2013.01); *G06T 7/60* (2013.01); *G06T 11/003* (2013.01); *G06T 19/20* (2013.01); *G16H 50/50* (2018.01); *A61B 6/5205* (2013.01); *G06T 2200/08* (2013.01); *G06T 2207/10081* (2013.01); *G06T 2207/10088* (2013.01); *G06T 2207/20076* (2013.01); *G06T 2207/30048* (2013.01); *G06T 2207/30096* (2013.01); *G06T 2207/30104* (2013.01); *G06T 2210/41* (2013.01)

(56) References Cited

U.S. PATENT DOCUMENTS

| | | |
|---|---|---|
| 2015/0065864 A1 | 3/2015 | Sharma et al. |
| 2015/0073722 A1* | 3/2015 | Taylor ................ A61B 5/02007 702/19 |
| 2015/0324962 A1 | 11/2015 | Itu et al. |
| 2015/0374243 A1* | 12/2015 | Itu ........................ G16H 50/50 703/2 |
| 2016/0022371 A1* | 1/2016 | Sauer .................... A61B 6/504 600/407 |
| 2016/0148372 A1* | 5/2016 | Itu ........................ G16H 50/50 382/128 |
| 2016/0166209 A1* | 6/2016 | Itu ........................ A61B 5/026 600/408 |
| 2016/0364860 A1* | 12/2016 | Taylor ................ A61B 5/02007 |

FOREIGN PATENT DOCUMENTS

| | | |
|---|---|---|
| WO | 2014/072861 A2 | 5/2014 |
| WO | 2015/082576 A1 | 6/2015 |
| WO | 2016/182508 A1 | 11/2016 |

OTHER PUBLICATIONS

Steinman et al., Reconstruction of carotid bifurcation hemodynamics and wall thickness using computational fluid dynamics and MRI. Magn Reson Med. Jan. 2002;47(1):149-59.

Zhang et al., Area Stenosis Associated with Non-Invasive Fractional Flow Reserve Obtained from Coronary CT Images. 35 Annual International Conference of the IEEE EMBS. pp. 3865-3868. Jul. 3-7, 2013.

Zhang et al., Hemodynamic analysis of patient-specific coronary artery tree. Int J Numer Method Biomed Eng. Feb. 2015;31(4):e02708. 16 pages.

International Search Report and Written Opinion for corresponding International Application No. PCT/SG2016/050213, dated Jun. 27, 2016. 8 pages.

* cited by examiner (a)

(b)

MEDICAL IMAGE PROCESSING METHODS AND SYSTEMS

RELATED APPLICATIONS

This application is a 35 U.S.C. § 371 national stage filing of International Application No. PCT/SG2016/050213, filed on May 6, 2016, which claims priority to Singapore Patent Application No. 10201503747W, filed on May 12, 2015. The entire contents of each of the foregoing applications are herein incorporated by reference.

FIELD OF THE INVENTION

Embodiments of the present invention relate to medical image processing. More specifically, embodiments disclosed herein relate to the processing of medical images of a coronary region of a patient to assess coronary stenosis by determining a fractional flow reserve (FFR).

BACKGROUND

Cardiovascular disease is the leading cause of death in both developed and developing countries. It accounts for 30% of all global deaths. Due to the aging population in the world, the number of patients with cardiovascular disease is expected to dramatically increase. Coronary artery disease (CAD) is the most prevalent cardiovascular disease, caused by the build-up of plaque inside the coronary artery. The plaque narrows the artery and eventually impacts the blood supply to the heart. As a result, CAD has been linked to the development of cardiovascular-related events and accounts for 45% of deaths due to cardiovascular disease.

Therefore characterization and quantification of the significance of coronary stenosis is of the utmost importance for patient management to prevent mortality from CAD. In clinical cardiology, both anatomical and hemodynamic indices are commonly applied to quantify the severity of CAD. The rapid developments of non-invasive imaging technologies, such as computed tomography angiography (CTA), are valuable, for their relatively lower cost and medical complications. Most of the non-invasive imaging technologies focus on anatomical significance and diameter stenosis (DS) is calculated as an index. DS expresses the diameter of a stenosed region relative to a "normal" segment, but it provides little or no hemodynamic information of the stenosis. The current gold standard to assess the functional severity of coronary artery stenosis is fractional flow reserve (FFR). FFR can be calculated as the ratio of the pressure distal to a coronary stenosis to aortic pressure at the hyperemia state. When the coronary stenosis leads to FFR≤0.80, revascularization is commonly recommended. However, FFR can only be measured via invasive coronary catheterization, which carries higher medical cost and some complications.

The limitations of invasive coronary catheterization motivates us to find a novel approach to assess the functional significance of coronary artery stenosis directly from medical images obtained with non-invasive imaging technologies.

In the current clinical practice, cardiologists and radiologists only have the anatomical information of the coronary artery stenosis from CTA images alone. There is a lack of information on the functional significance of the coronary lesion. However, anatomical index of diameter stenosis (DS) was found to lead to a much higher false positive rate relative to FFR and tends to overestimate the significance of the stenosis for ischemia.

SUMMARY OF THE INVENTION

According to a first aspect of the present invention there is provided a medical image processing method of determining a fractional flow reserve through a stenosis of a coronary artery from medical image data. The medical image data comprises a set of images of a coronary region of a patient. The coronary region includes the stenosis. The method comprises: reconstructing a three dimensional model of a coronary artery tree of the patient from the medical image data; determining stenosis dimensions from the three dimensional model of the coronary artery tree of the patient; simulating blood flow in the three dimensional model of the coronary artery tree of the patient to determine modeled flow rates; using an analytical model depending on the stenosis dimensions to predict a modeled pressure drop over the stenosis from the modeled flow rates; and determining the fractional flow reserve through the stenosis from the modeled pressure drop.

Embodiments of the present invention may utilize an analytical model to allow real-time computation of FFR, according to stenosis dimensions (proximal, distal and minimal lumen area, and length) and hyperemic coronary flow rate through the lesion. As the stenosis dimensions can be obtained via non-invasive CTA and computational fluid dynamics (CFD) could help to derive the hyperemic coronary flow rate through the lesion. It is feasible to build up a framework for analyzing hemodynamic significance of coronary artery stenosis with the analytical model.

In an embodiment simulating blood flow in the three dimensional model of the coronary artery tree of the patient to determine modeled flow rates comprises simulating steady state blood flow. The simulation of steady state blood flow may comprise iteratively determining steady state fluid resistance and pressure values.

Embodiments of the present invention use simplified computational fluid dynamics (CFD) that may involve using steady state flow simulation and/or novel boundary conditions to reduce the complexity of pulsatile flow simulation with reduced-order models as boundary conditions.

In an embodiment, the iterative determination of steady state fluid resistance and pressure values comprises iteratively updating the steady state fluid resistance and pressure values with an under-relaxation scheme.

In an embodiment the three dimensional model of the coronary artery tree of the patient data comprises at least one inlet and a plurality of outlets, and the method further comprises estimating a total inlet flow into the three dimensional model of the coronary artery tree of the patient from the medical image data and wherein iteratively determining steady state fluid resistance and pressure values comprises iteratively updating the steady state fluid resistance and pressure values until a total outlet flow from the plurality of outlets matches the total inlet flow.

The simulated blood flow may be hyperemic blood flow. Hyperemic flow refers to a physiological state, when the resistance of downstream vessels becomes minimal and the blood flow through coronary vessel becomes maximum. It relates to the flow conditions targeted to model with either steady state flow or pulsating flow.

In an embodiment, the using the analytical model depending on the stenosis dimensions to predict a modeled pressure drop over the stenosis from the modeled flow rates comprises determining a radius of inviscid core depending on a stenosis length and a flow rate and comparing the radius of inviscid core with a threshold to determine whether to include an entrance effect in the analytical model.

In an embodiment the analytical model is based upon a modified version of the Bernoulli equation.

According to a further aspect of the present invention there is provided a method of assessing the functional significance of coronary artery stenosis from medical image data. The method comprises determining a fractional flow reserve through a stenosis of a coronary artery from the medical image data according to the method an embodiment described above; and comparing the fractional flow reserve through the stenosis of the coronary artery with a threshold to assess the functional significance of the coronary artery stenosis.

In an embodiment comparing the fractional flow reserve through the stenosis of the coronary artery with a threshold to assess the functional significance of the coronary artery stenosis comprises classifying the stenosis as an ischemic lesion if the fractional flow reserve through the stenosis of the coronary artery is less than the threshold.

In an embodiment comparing the fractional flow reserve through the stenosis of the coronary artery with a threshold to assess the functional significance of the coronary artery stenosis comprises classifying the stenosis as a non-ischemic lesion if the fractional flow reserve through the stenosis of the coronary artery is greater than the threshold. In an embodiment the threshold is 0.8.

According to a further aspect of the present invention there is provided a medical image processing system for determining a fractional flow reserve through a stenosis of a coronary artery from medical image data. The medical image data comprises a set of images of a coronary region of a patient. The coronary region includes the stenosis. The system comprises a computer processor and a data storage device, the data storage device having a three dimensional model reconstruction module; a stenosis dimension determination module; a blood flow simulation module; an analytical modeling module; and a fractional flow reserve determination module comprising non-transitory instructions operative by the processor to: reconstruct a three dimensional model of a coronary artery tree of the patient from the medical image data; determine stenosis dimensions from the three dimensional model of the coronary artery tree of the patient; simulate blood flow in the three dimensional model of the coronary artery tree of the patient to determine modeled flow rates; use an analytical model depending on the stenosis dimensions to predict a modeled pressure drop over the stenosis from the modeled flow rates; and determine the fractional flow reserve through the stenosis from the modeled pressure drop.

According to a yet further aspect, there is provided a non-transitory computer-readable medium. The computer-readable medium has stored thereon program instructions for causing at least one processor to perform operations of a method disclosed above.

BRIEF DESCRIPTION OF THE DRAWINGS

In the following, embodiments of the present invention will be described as non-limiting examples with reference to the accompanying drawings in which.

DETAILED DESCRIPTION

Figure 1:
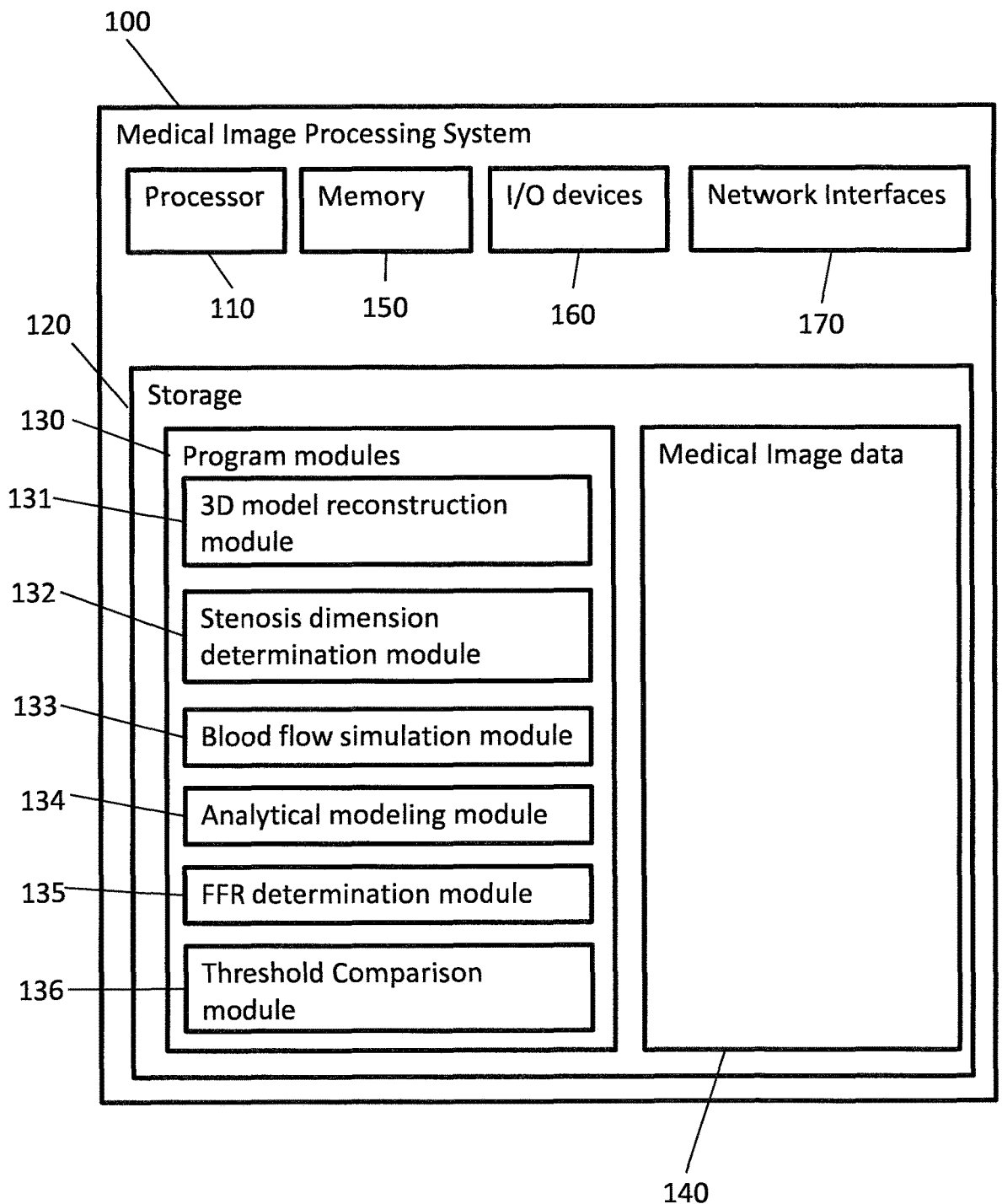
FIG. 1 is a block diagram showing a medical image processing system according to an embodiment of the present invention.

FIG. 1 shows a medical image processing system according to an embodiment of the present invention. The image processing system 100 comprises a processor 110 which may be referred to as a central processing unit (CPU) that is in communication with memory devices including storage 120 and memory 150. The Processor 110 may be implemented as one or more CPU chips. The memory 150 is implemented as a random access memory (RAM). The medical image processing system further comprises input/output (I/O) devices 160 and network interfaces 170.

The storage 120 typically comprises one or more disk drives and is used for non-volatile storage of data. The storage 120 stores program modules 130 which are loaded into the memory 150 when such programs are selected for execution. The program modules comprise a 3D model reconstruction module 131; a stenosis dimension determination module 132; a blood flow simulation module 133; an analytical modeling module 134; a fractional flow reserve (FFR) determination module 135 and a threshold comparison module 136. Each of the program modules 130 stored in the storage 120 comprises non-transitory instructions operative by the processor 120 to perform the various operations in the methods described in more detail below. The storage 120 and the memory 150 may be referred to in some contexts as computer readable storage media and/or non-transitory computer readable media.

The storage 120 also stores medical image data 140. The medical image data comprises a set of medical images of a coronary region of a patient. The coronary region of the patient may include a stenosis which is under analysis by the methods described below. The medical image data 140 may be in the DICOM format. The medical image data may be obtained through a medical imaging technique such as a computed tomography (CT) scan of the patient, a computed tomography angiography (CTA) scan; or a magnetic resonance imaging (MRI) scan of the patient.

The I/O devices 160 may include printers; video monitors; liquid crystal displays (LCDs); plasma displays; touch screen displays keyboards; keypads; switches; dials; mice; track balls; voice recognizers; card readers; or other well-known input devices.

The network interfaces 170 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network interfaces 170 may enable the processor 110 to communicate with the Internet or one or more intranets. With such a network connection, it is contemplated that the processor 110 might receive information from the network, or might output information to the network in the course of performing the below-described method operations. Such information, which is often represented as a sequence of instructions to be executed using processor 110, may be received from and outputted to the network, for example, in the form of a computer data signal embodied in a carrier wave.

The network interfaces 170 may allow the medical image processing system 110 to receive the medical image data 140 from a medical imaging apparatus for processing according an the method described below.

The processor 110 executes instructions, codes, computer programs, scripts which it accesses from hard disk, floppy disk, optical disk (these various disk based systems may all be considered storage 120), flash drive, memory 150, or the network interfaces 170. While only one processor 110 is shown, multiple processors may be present. Thus, while instructions may be discussed as executed by a processor, the instructions may be executed simultaneously, serially, or otherwise executed by one or multiple processors.

It is understood that by programming and/or loading executable instructions onto the medical image processing system 100, at least one of the CPU 110, the memory 150, and the storage 120 are changed, transforming the image processing system in part into a specific purpose machine or system having the novel functionality taught by the present disclosure. It is fundamental to the electrical engineering and software engineering arts that functionality that can be implemented by loading executable software into a computer can be converted to a hardware implementation by well-known design rules.

Although the system 100 is described with reference to a computer, it should be appreciated that the system may be formed by two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, the functionality disclosed above may be provided by executing the application and/or applications in a cloud computing environment. Cloud computing may comprise providing computing services via a network connection using dynamically scalable computing resources. A cloud computing environment may be established by an enterprise and/or may be hired on an as-needed basis from a third party provider.

Figure 2:
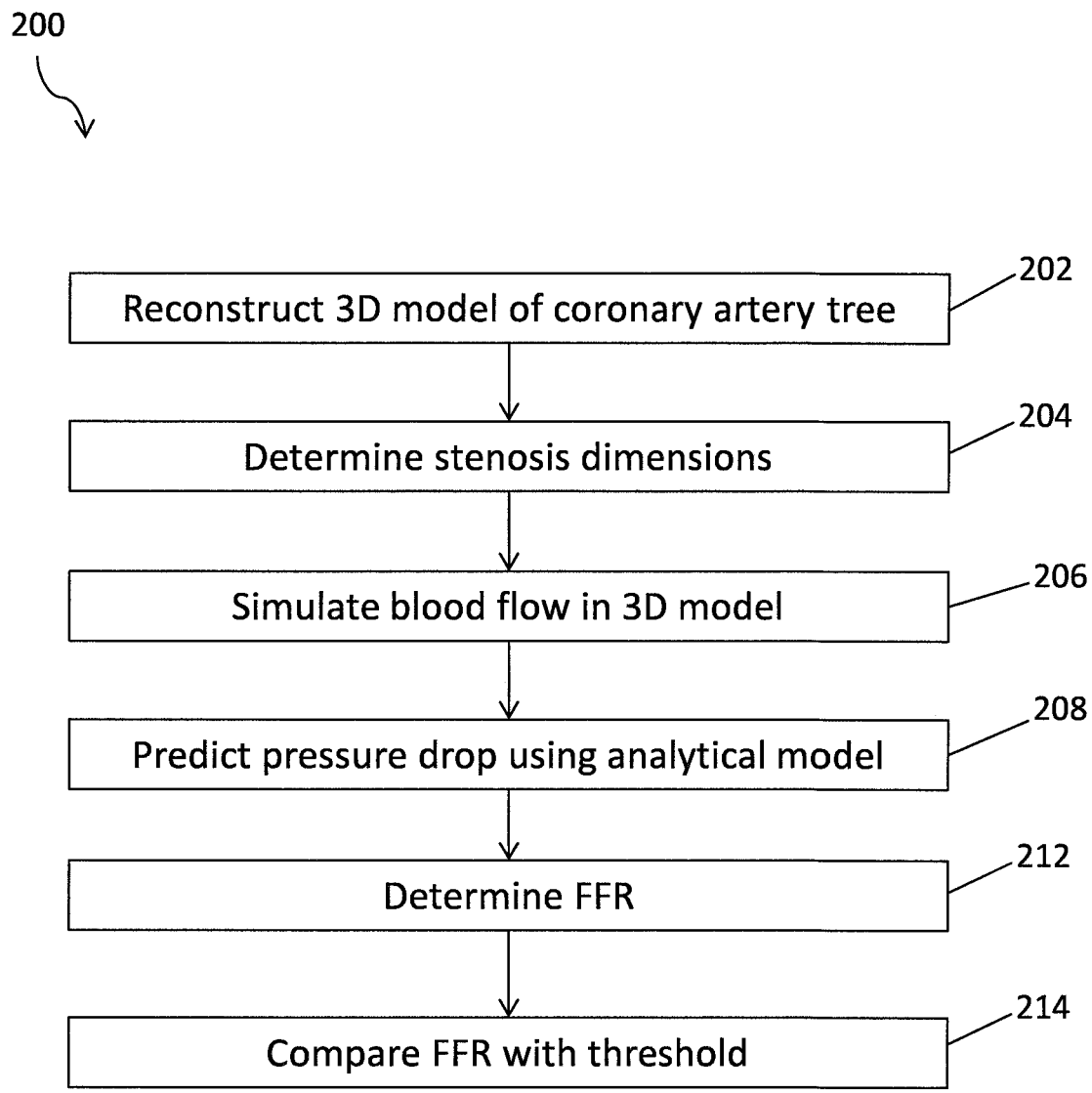
FIG. 2 is a flow chart illustrating a method of processing medical image data according to an embodiment of the present invention.

FIG. 2 is a flow chart illustrating a method of processing medical image data according to an embodiment of the present invention. The method 200 of figure may be performed on the medical image processing system 100 shown in FIG. 1. It should be noted that enumeration of operations is for purposes of clarity and that the operations need not be performed in the order implied by the enumeration.

As described above, the method 200 is carried out on medical image data 140. The medical image data 140 may be obtained through standard coronary CTA as described in the following example. Standard coronary CTA was performed using a 64 slice multi-detector CTA scanner (such as a Toshiba Aquilion 64, having 0.5 mm×64 detector row) or a 320 slice multi-detector CTA scanner (Toshiba Aquilion ONE™ having 0.5 mm×320 detector row) following current clinical guidelines. The scanning range was planned individually to cover the major coronary arteries and aorta. Beta-blocker was administrated some patients to moderate heart rate. Omnipaque non-Ionic contrast medium was routinely given before image acquisition to highlight regions of interest in the CT images. The dose of contrast was controlled by using electrocardiographic triggering prospectively. Image acquisition was performed with an inspiratory breath-hold. The scan parameters were gantry rotation time at 350-400 ms, tube potential at 100-120 kV and field of view (FOV) at 161-230 mm. Depending on the cardiac dimensions and pitch, scanning time was 5.7-8.4 s for a single breath hold in the craniocaudal direction. All CT images were recorded with 0.25 mm increment (i.e., 0.5 mm slice thickness) and saved in 'DICOM' format for image processing.

In step 202, the 3D reconstruction module 131 of the medical image processing system 100 reconstructs a three dimensional model of the coronary artery tree of the patient from the medical image data 140. In step 202, Image processing may be performed to segment the artery structure from the background CT image for reconstructing the 3D coronary artery tree. At first, a Hessian matrix-based filter is applied to each single transverse CT image to obtain high order geometric characteristics; i.e., the principal curvature of image intensity. Eigenvector analysis of the Hessian matrix obtained is used to determine whether the voxel under analysis belongs to the vessel structure or not. Finally, a graph-cuts based image segmentation technique is applied to the enhanced 3D image, before using a marching cube algorithm to establish the triangulated surface mesh from the segmented voxel data. It was found that manual editing was necessary for some models to remove artifacts and small vessels with diameters <1 mm.

In step 204, the stenosis dimension determination module 132 of the medical image processing system 100 determines dimensions of the stenosis from the three dimensional model of the artery tree reconstructed in step 202. The stenosis dimensions, such as proximal, distal and minimal lumen area, and length can be measured through the reconstructed 3D model.

In step 206, the blood flow simulation module 133 of the medical image processing system 100 simulates blood flow in the three dimensional model. In step 206, for the 3D model, computation fluid dynamics (CFD) is performed to obtain the hyperemic coronary flow rate through the lesion. In order to non-invasively obtain the flow rate information of the coronary lesion, CFD simulation was performed. At first, the 3D coronary model was discretized to separate the computational domain into small control volumes. And then, morphology and physiology based boundary conditions were set to the boundaries. After that, the conservation equations of mass and momentum were solved by iterations. Finally, the flow rate information was retrieved from the solutions.

In step 206, ANSYS workbench, a commercial software package may be used to discretize the computational domain into tetrahedral shaped elements. After a mesh dependency test, the coronary artery tree model was discretized with a total of about 0.8 million volume cells. Further grid refinement led to <1% relative error in maximum velocity.

In an embodiment, FLUENT™ was used to solve continuity and Navier-Stokes equations. Blood was modeled as Newtonian fluid to simulate blood flow in the patient-specific coronary artery tree models. Appropriate boundary conditions were specified at the inlet and outlets of each model respectively to mimic physiological conditions, and satisfy 3 key principles. First, coronary supply was assumed to meet myocardial demand at rest. Hence, resting total coronary blood flow rate can be calculated from myocardial mass which were assessed from CT images. Second, the resistance of each coronary branch at rest was proportional to the size of parent and child branch vessels. Third, coronary resistance was assumed to reduce predictably during hyperemia conditions, which was within the expected physiological range.

To simulate blood flow in the patient-specific coronary artery tree models, this study used FLUENT™ to solve continuity and Navier-Stokes equations as shown in Eqs. (1) and (2) respectively.

$$\frac{\partial u_j}{\partial x_j} = 0 \tag{1}$$

$$\rho \frac{\partial (u_j u_i)}{\partial x_j} = -\frac{\partial P}{\partial x_i} + \mu \frac{\partial}{\partial x_j}\left(\frac{\partial u_i}{\partial x_j} + \frac{\partial u_j}{\partial x_i}\right) \tag{2}$$

where $x_j$ is the location in Cartesian coordinates, $u_j$ (or $u_i$) is the Cartesian component of velocity, P represents the static pressure; and ρ and ρ were set as 1,060 kg/m³ and 4.5×10−3 Pa·s respectively to represent the density and dynamic viscosity of blood in large epicardial arteries.

Pressure and resistance boundary conditions were specified at the inlet and outlets of each model respectively to mimic physiological conditions. To assign the inlet total pressure, patient-specific systolic and diastolic brachial pressure was used to calculate the mean brachial pressure and match the mean aortic pressure.

A key element in assigning coronary resistance values of the outlets is to prescribe reference pressure ($P_0$). Physiologic studies report that coronary pressure flow lines are concave to the axis of flow at lower pressures but straight at physiological pressures. The zero flow pressure intercept at the physiologic pressure range (i.e., $P_0$ in this disclosure) exceeds coronary venous or left ventricular diastolic pressure by five to ten-fold. Therefore, we propose a novel method in this study to determine the reference pressure $P_0$, and therefore outlet resistances through an iterative procedure. The details are provided as following. Briefly, the total resistance $R_{inlet}$ at resting condition is defined by Eq. (3).

$$R_{inlet}(P_{inlet} - P_0)/Q_{inlet} \tag{3}$$

where $P_{inlet}$ represents the mean aortic pressure, estimated from the mean branchial artery pressure. The total coronary flow at resting can be estimated from the myocardial mass. Accordingly $Q_{inlet}$ can be determined from CT images.

At each coronary outlet, $$P_i = P_0 + R_i Q_i \tag{4}$$

The correlation between the resistance of downstream vasculature of each coronary branch $R_i$ and that of the coronary tree $R_{inlet}$ can be estimated from the scaling law of equation (5) below.

$$R_i = N_i R_{inlet} \tag{5}$$

Here, $N_i$ represents the ratio of flow rate at inlet to the $i^{th}$ outlet. From (3) and (5), $R_i$ can have the following form:

$$R_i = N_i \frac{P_{inlet} - P_0}{Q_{inlet}} \tag{6}$$

By the mass conservation law, total outflow was equal to inflow (Eq. (7)), $$\sum_{i=1}^{N} Q_i = Q_{inlet} \tag{7}$$

From Eqs. (4), (5) and (7), it can be shown that $P_0$ is given by:

$$P_0 = P_{inlet} - \sum_{i=1}^{N} \left(\frac{P_i - P_0}{N_i}\right) \tag{8}$$

At hyperemia, coronary microcirculation was assumed to have predictable response to adenosine and the resistance was assumed to be reduced to K times the resting values (where K=0.21), a value within the expected physiological range.

From Eq. (6), the hyperemic resistance is given by:

$$R_{i,hyperemia} = KR_i = KN_i \frac{P_{inlet} - P_0}{Q_{inlet}} \tag{9}$$

In order to ensure smooth convergence during the numerical iterations of CFD, $P_0$ and $R_i$ were initialized as 20 mmHg and 1.0e+8 Pa·s/m3, respectively; and then updated with a under-relaxation scheme as formulated in Eqs. (10) and (11) until the total outflow from all the outlets matched the inflow rate at hyperemia.

$$P_{0,new} = (1-\alpha)P_{0,old} + \alpha\left(P_{inlet} - \sum_{i=1}^{N}\left(\frac{P_i - P_0}{N_i}\right)\right) \tag{10}$$

$$R_{i,hyperemia,new} = (1-\alpha)R_{i,hyperemia,old} + \alpha\left(KN_i \frac{P_{inlet} - P_0}{Q_{inlet}}\right) \tag{11}$$

Here, α is an under-relaxation factor. $P_{0,old}$ and $R_{i,hyperemia,old}$ represent the reference pressure and resistance in the last iteration, while $P_{0,new}$ and $R_{i,hyperemia,new}$ represent their values in the next iteration. As minimal microvascular resistance has been found to be independent of epicardial stenosis severity, hyperemic microcirculatory resistance distal to a stenosis was assumed to be the same as that for coronary arteries free of stenosis as specified in Eq. (11).

With these novel iterative boundary conditions, the computational burden can be reduced in contrast to solving the complex lumped-parameter heart and coronary models.

The calculated value of $P_0$ was 38.6±9.5 mmHg for 21 patients investigated in this study, which was close to 37.9±9.8 mmHg measured by Dole et al. (Dole W P, Richards K L, Hartley C J, Alexander G M, Campbell A B, Bishop V S. Diastolic coronary artery pressure-flow velocity relationships in conscious man. Cardiovasc Res. 1984; 18(9): 548-554) for 10 patients and 36±9 mmHg measured by Nanto et al. (Nanto S, Masuyama T, Takano Y. Determination of coronary zero flow pressure by analysis of the baseline pressure—flow relationship in humans. Jpn Circ J. 2001; 65 (9): 793-796) for 15 subjects respectively at vasodilated state. A no-slip boundary condition was imposed on the vessel wall.

In step 208, the analytical modelling module 134 of the medical image processing system 100 predicts the pressure drop across a stenosis lesion using an analytical model. According to the stenosis dimensions, such as proximal, distal and minimal lumen area, and length measured from the reconstructed 3D model and flow rate information obtained from CFD simulation, analytical analysis is performed according to the method described below.

We used an analytical model to predict the pressure drop over a stenosis ($\Delta P_1$). As longer stenosis led to larger pressure drop due to entrance effects, a dimensionless radius of inviscid core ($\gamma$) was first solved with Eq. 12 to determine whether to include the entrance effect as:

$$\frac{\pi \mu L}{4\rho Q} = \frac{1}{4}\int_\gamma^1 \frac{(1-\gamma)(6+\gamma)(1+4\gamma+9\gamma^2+4\gamma^3)}{5\gamma(3+2\gamma)(3+2\gamma+\gamma^2)^2} d\gamma \quad (12)$$

L and Q represent the stenosis length and flow rate, respectively. $\mu$ and $\rho$ were the viscosity and density of the blood.

If $\gamma \geq 0.05$, the stenosis length was short and the entrance effect can be ignored. Therefore, the pressure drop in a vessel with a single stenosis can be calculated as follows:

$$\Delta P_1 = \frac{\rho Q^2}{2}\left(\frac{1}{A_{distal}^2} - \frac{1}{A_{proximal}^2}\right) + \quad (13)$$
$$\frac{\rho Q^2}{2 A_{stenosis}^2} \frac{96}{5} \times \int_\gamma^1 \frac{(1+4\gamma+9\gamma^2+4\gamma^3)}{\gamma(3+2\gamma)(3+2\gamma+\gamma^2)^2} d\gamma +$$
$$\frac{\rho Q^2}{2}\left\{\left(\frac{1}{A_{stenosis}} - \frac{1}{A_{distal}}\right)^2 + \left[2\left(\frac{1}{A_{stenosis}} - \frac{1}{A_{distal}}\right)\right.\right.$$
$$\left.\left.\left(\frac{1}{A_{stenosis}} - \frac{1}{3A_{distal}}\right) - \left(\frac{1}{A_{stenosis}} - \frac{1}{A_{distal}}\right)^2\right](1-\gamma)^2\right\}$$

$A_{distal}$, $A_{proximal}$ and $A_{stenosis}$ represent the lumen area at the distal, proximal and stenotic locations, respectively.

For long stenoses ($\gamma < 0.05$), the entrance effect was considered and the total pressure drop over a single stenosis was calculated as:

$$\Delta P_1 = \frac{\rho Q^2}{2}\left(\frac{1}{A_{distal}^2} - \frac{1}{A_{proximal}^2}\right) + \quad (14)$$
$$\frac{\rho Q^2}{2 A_{stenosis}^2} \frac{96}{5} \times \int_{0.05}^1 \frac{(1+4\gamma+9\gamma^2+4\gamma^3)}{\gamma(3+2\gamma)(3+2\gamma+\gamma^2)^2} d\gamma +$$
$$\rho Q^2 \left(\frac{1}{A_{stenosis}} - \frac{1}{A_{distal}}\right) \times \left(\frac{1}{A_{stenosis}} - \frac{1}{3A_{distal}}\right)$$

As described above, the analytical model was derived from energy conservation which considered the convection and diffusive energy losses as well as the energy loss due to sudden constriction and expansion in lumen area. In this disclosure, the hyperemic coronary flow rate through the coronary branches was specified with the data obtained from simulation. Together with the dimensions (proximal, distal and minimal lumen area, and length) of the stenosis, the pressure drop over a stenosis ($\Delta P_1$) was derived according to the analytical model. The pressure drop over the normal vessel segments (from the inlet to the segment before stenosis), $\Delta P_2$, was calculated according to Poiseuille equation.

In step 210, the FFR determination module 135 of the medical image processing system 100 determines the FFR using the following equation:

$$FFR_B = 1 - \frac{\Delta P_1 + \Delta P_2}{P}$$

Where P represents patient-specific mean aortic pressure. In this disclosure, the FFR calculated by this method is denoted $FFR_B$ to indicate that the FFR is calculated using modified Bernoulli equations (13) and/or (14) described above.

In step 212, the threshold comparison module 136 of the medical image processing system 100 compares the calculated FFR with a threshold to classify the stenosis. If a lesion led to $FFR_B \leq 0.8$, the stenosis was classified as an ischemic lesion. Conversely, a lesion with $FFR_B > 0.8$ was classified as non-ischemic.

Figure 3:
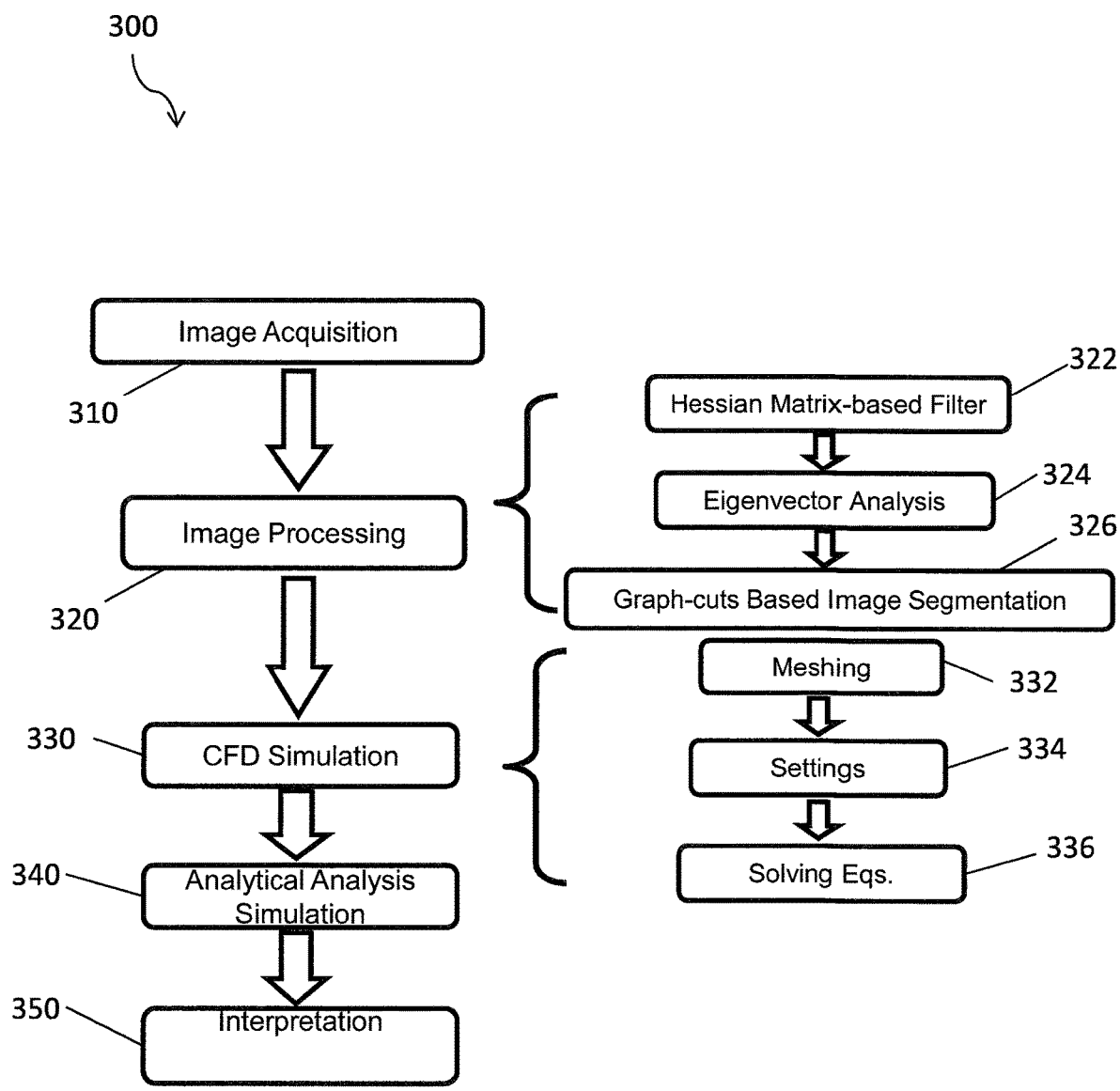
FIG. 3 is a flowchart showing a method of assessing functional significance of coronary artery disease according to an embodiment of the present invention.

FIG. 3 is a flowchart showing a method of assessing functional significance of coronary artery disease according to an embodiment of the present invention.

As described above, the method 300 relates to a computer-aided technique and method for analyzing CTA images and assessing functional significance of coronary artery disease. The method 300 includes CTA image acquisition 310, CTA image processing 320, CFD simulation 330 and analytical analysis 340. After acquisition of the CTA images through CTA scanner, image processing 330 was performed to reconstruct 3D coronary artery tree. In order to process the CTA images, Hessian matrix-based filter 322, eigenvector analysis 324 and graph-cuts based image segmentation 326 techniques were applied. The stenosis dimensions, such as proximal, distal and minimal lumen area, and length can be measured through the reconstructed 3D model.

For the 3D model, steady-flow CFD was performed to obtain the hyperemic coronary flow rate through the lesion. A typical CFD simulation 330 comprises meshing 332 (to discretize the computational domain into small control volumes), setting morphology and physiology-based boundary conditions 334, solving the mass and momentum conservation equations 336 and post-processing.

Finally, analytical analysis 340 was implemented to compute $FFR_B$, with stenosis dimensions (proximal, distal and minimal lumen area, and length) and hyperemic coronary flow rate through the lesion.

As described above, in an embodiment the may be considered to contain four steps: image acquisition 310, image processing 320, CFD simulation 330 and analytical analysis 340. The preferred mode of practice of the invention could be implemented by many advanced programming languages including Matlab, C/C++.

In the image acquisition step 310, the CT images were obtained in the clinical practice. The images conform to the DICOM protocol. Meta information of all images were inspected and recorded.

In the image processing step 320, in order to reconstruct the 3D coronary artery tree, image processing was performed to segment the artery structure from the background CT images. At first, a Hessian matrix-based filter 332 was applied to each single transverse CT image to obtain high order geometric characteristics. After that, the eigenvector of the obtained Hessian matrix was analyzed 324 to determine whether the voxel under analysis belonged to the vessel structure or not. Finally, the graph-cuts based image segmentation technique 326 and marching cube algorithm were used to generate the 3D surface and volume meshes.

On the reconstructed 3D model, the stenosis dimensions, such as proximal, distal and minimal lumen area, and length can be measured, DS of the stenosis was calculated.

In the CFD simulation step 330, a steady flow CFD simulation is carried out. In order to non-invasively obtain the flow rate information of the coronary lesion, CFD simulation was performed. At first, the 3D coronary model was discretized in the meshing step 332 to separate the computational domain into small control volumes. And then, morphology and physiology based boundary conditions were set in the setting step 334 to the boundaries. After that, the conservation equations of mass and momentum were solved by iterations. Finally, the flow rate information was retrieved from the solutions in step 336.

In the analytical analysis step 340, according to the stenosis dimensions, such as proximal, distal and minimal lumen area, and length measured from the reconstructed 3D model and flow rate information obtained from CFD simulation, analytical analysis was performed according to obtain hemodynamic index of $FFR_B$.

In the interpretation step 350, the value of FFR is compared with a threshold. If a lesion led to $FFR_B \leq 0.8$, the stenosis was classified as an ischemic lesion. Conversely, a lesion with $FFR_B > 0.8$ was classified as non-ischemic.

Figure 4:
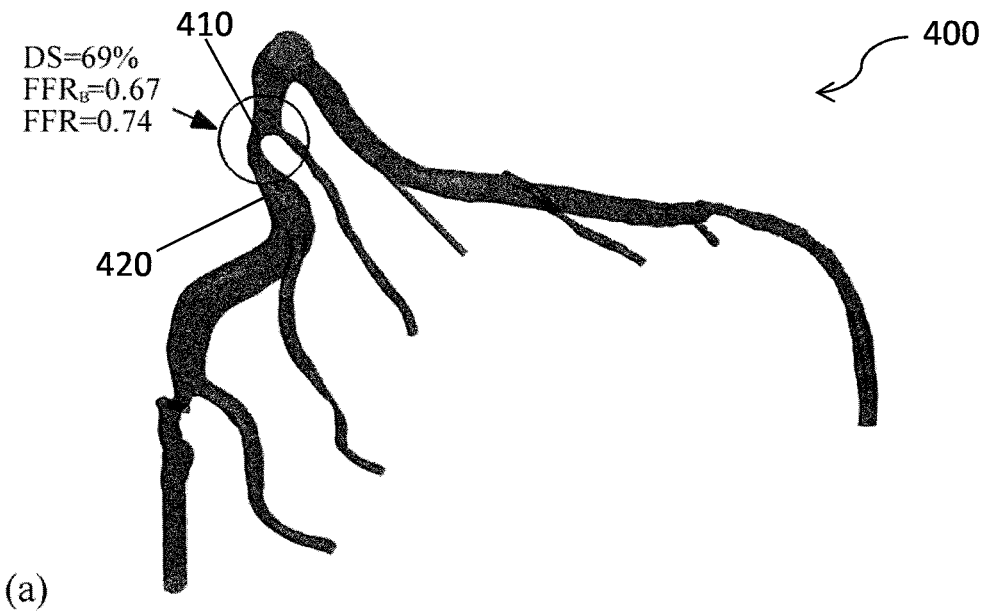
FIGS. 4a and 4b show examples of application of the methods according to embodiments of the present invention to medical image data for two patients with ischemia coronary artery lesions.
Figure 4:
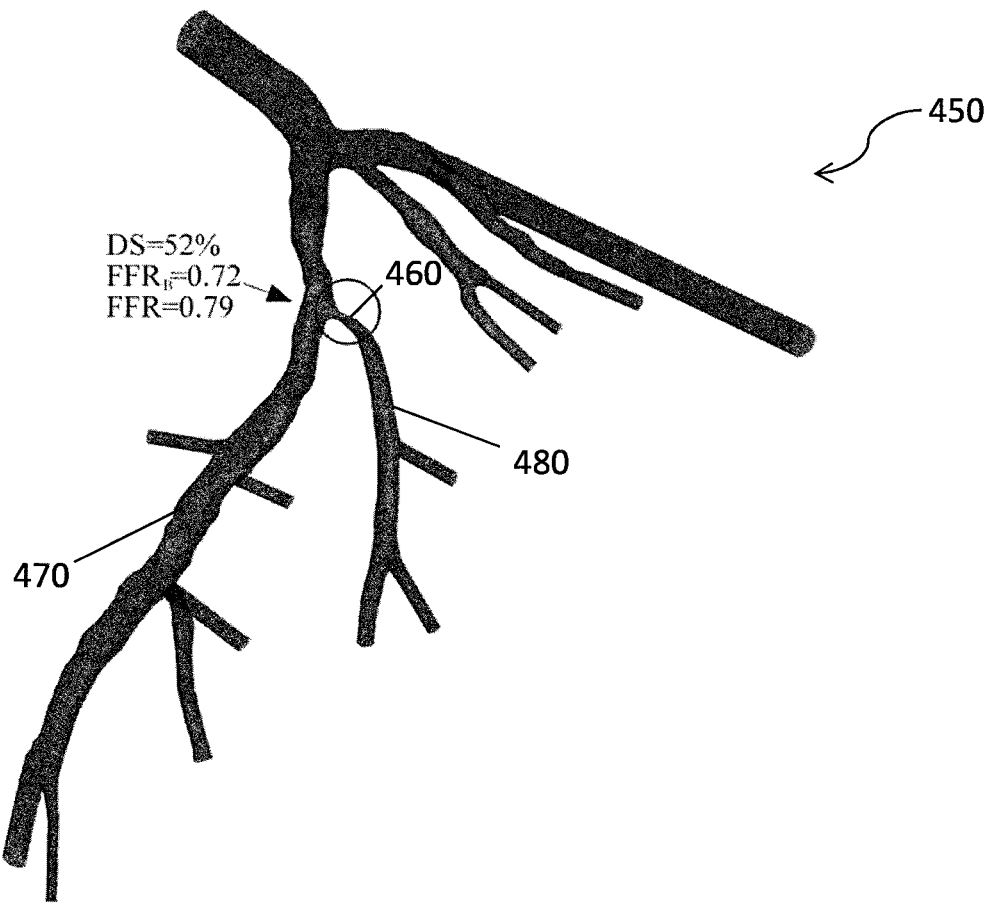

FIGS. 4a and 4b show examples of application of the methods described above to medical image data for two patients with ischemia coronary artery lesions.

As shown in FIG. 4a, one patient 400 has an ischemia lesion 410 along the mid left anterior descending artery (LAD) 420.

As shown in FIG. 4b, one patient 450 has an ischemia lesion 460 along the first diagonal 480 of the LAD 470.

FIGS. 4a and 4b also show the calculated anatomical index of diameter stenosis (DS); the fractional flow reserve, $FFR_B$ calculated using a method according to an embodiment of the present invention as described above, and the fractional flow reserve FFR measured via invasive coronary catheterization. For the patient shown in FIG. 4a, the DS was calculated as 69%; the $FFR_B$ was calculated as 0.67 and the FFR was measured as 0.74. For the patient shown in FIG. 4b, the DS was calculated as 52%; the $FFR_B$ was calculated as 0.72 and the FFR was measured as 0.79.

Figure 5:
FIGS. 5a and 5b show examples of application of the methods according to embodiments of the present invention to medical image data for two patients with non-ischemia coronary artery lesions.
Figure 5:
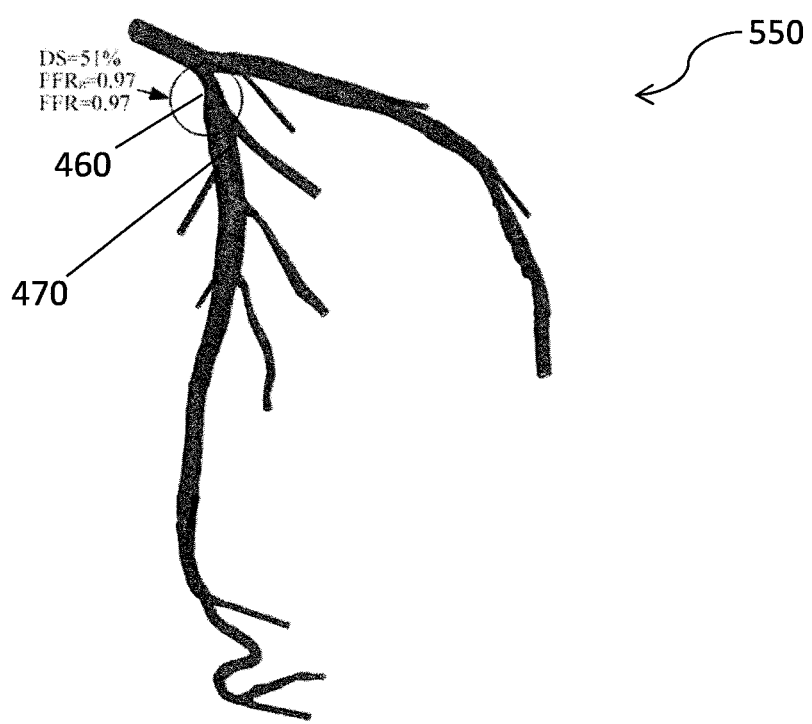

FIGS. 5a and 5b show examples of application of the methods described above to medical image data for two patients with non-ischemia coronary artery lesions.

As shown in FIG. 5a, one patient 500 has a non-ischemia lesion 510 along the mid LAD 520.

As shown in FIG. 5b, one patient 550 has a non-ischemia lesion 460 along the proximal LAD 570.

FIGS. 5a and 5b also show the calculated anatomical index of diameter stenosis (DS); the fractional flow reserve, $FFR_B$ calculated using a method according to an embodi-
ment of the present invention as described above, and the fractional flow reserve FFR measured via invasive coronary catheterization. For the patient shown in FIG. 5a, the DS was calculated as 61%; the $FFR_B$ was calculated as 0.89 and the FFR was measured as 0.83. For the patient shown in FIG. 5b, the DS was calculated as 51%; the $FFR_B$ was calculated as 0.97 and the FFR was measured as 0.97.

As shown in FIGS. 4a, 4b, 5a and 5b, all the non-invasively derived hemodynamic index of $FFR_B$ with present invention was close to FFR measured via invasive angiography. The two patients having non-ischemic lesion had DS values larger than 50%, which demonstrated that DS may lead to false positive prediction. The hemodynamic indices of $FFR_B$ were of the utmost importance to assess the functional significance of coronary artery disease non-invasively.

To validate the invention, we carried out a pilot-study; 21 patients were recruited and they underwent CTA and invasive angiography subsequently for diagnosing CAD. FFR was measured for a total of 32 vessels.

Figure 6A:
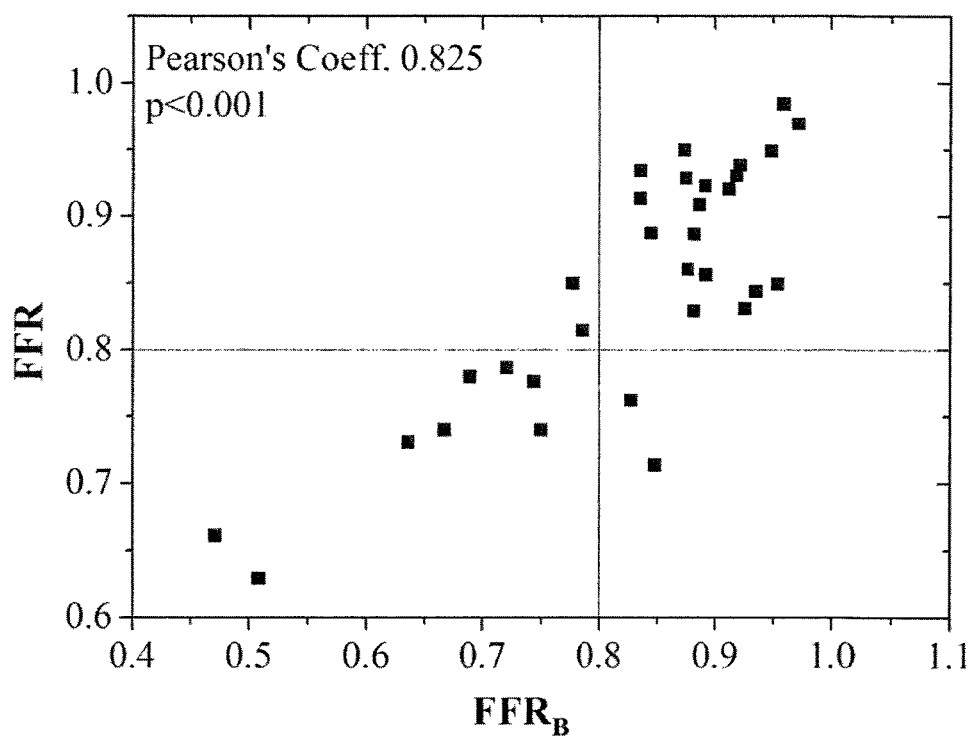
FIG. 6a is a graph showing correlation between measured $FFR_B$ and FFR calculated using a method according to an embodiment of the present invention.

FIG. 6a is a plot showing correlation between the measured FFR and the calculated $FFR_B$. As shown in FIG. 6a, the calculated $FFR_B$ had a good correlation with FFR ($R=0.825$, $p<0.001$).

Figure 6B:
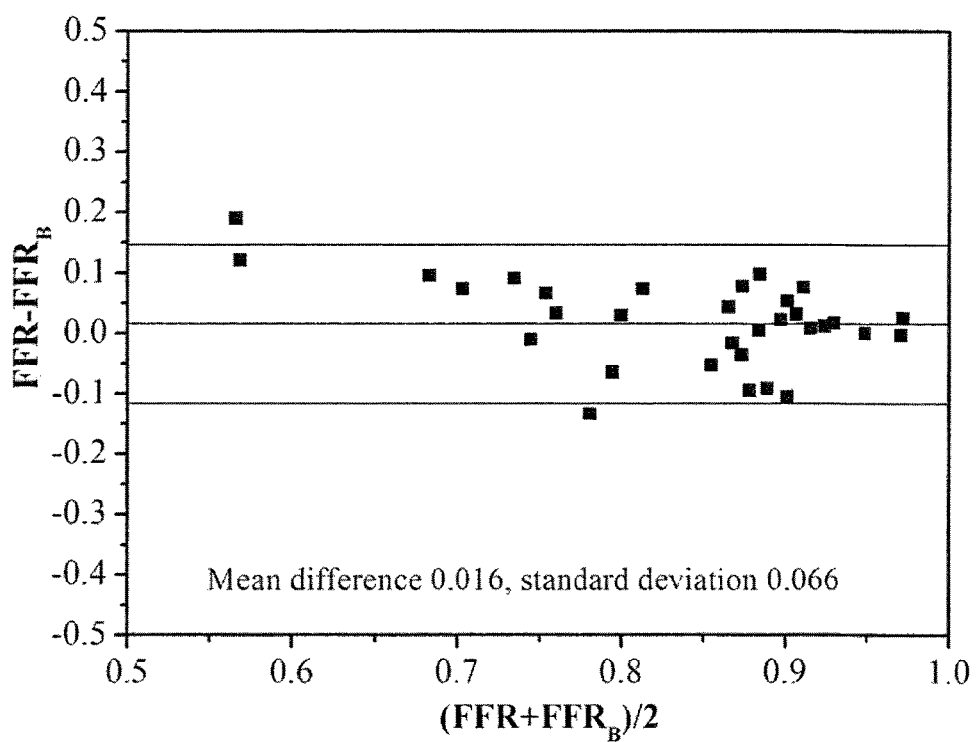
FIG. 6b is a graph showing a Bland-Altman Plot of the measured $FFR_B$ and FFR calculated using a method according to an embodiment of the present invention on a Per-Vessel basis.

FIG. 6b is a Bland-Altman Plot of the measured FFR and the calculated $FFR_B$ on a Per-Vessel basis. As shown in FIG. 6b, the difference between FFR and $FFR_B$ were negligible.

Figure 7:
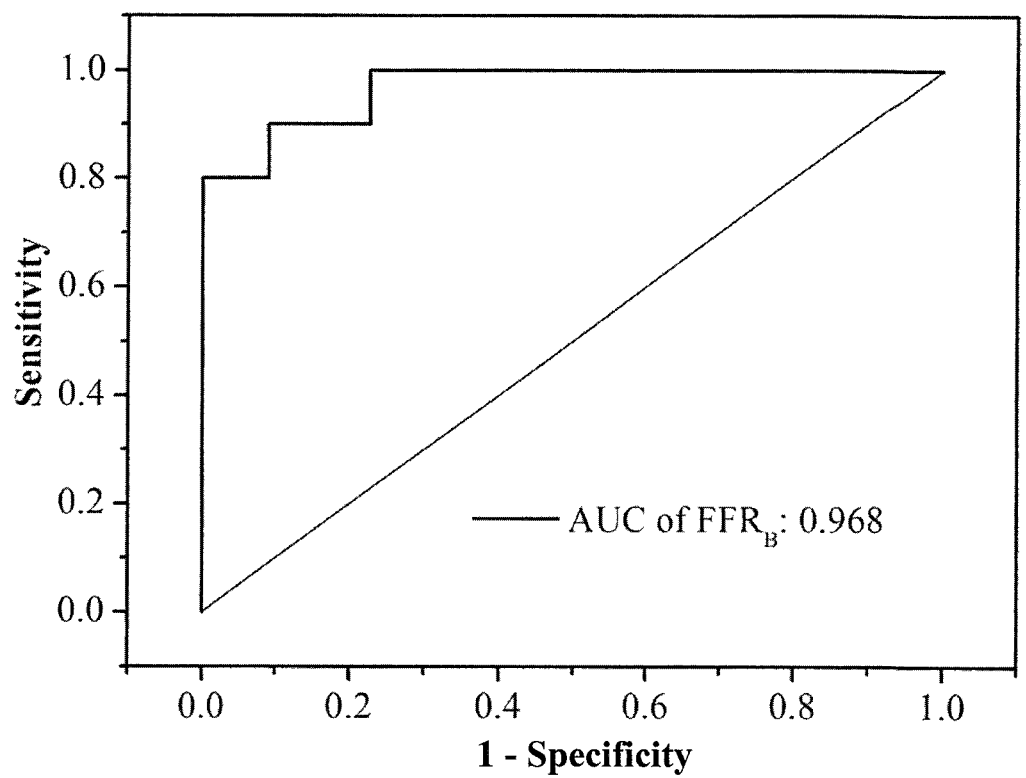
FIG. 7 is graph showing area under the curve of per vessel performance for an embodiment of the present invention.

FIG. 7 is an area under the curve (AUC) curve of per vessel performance for $FFR_B \leq 0.8$. Areas under the receiver-operating characteristic (AUC) of FFRB was 0.968 on a per-vessel level.

Diagnostic accuracy, positive predictive value (PPV), negative predictive value (NPV), sensitivity and specificity for $FFR_B$ on a per-vessel basis were 87.5%, 80.0%, 90.9%, 80.0% and 90.9%, respectively. Overall, $FFR_B$ is a promising index to diagnose the hemodynamic significance of coronary stenosis.

Whilst the foregoing description has described exemplary embodiments, it will be understood by those skilled in the art that many variations of the embodiments can be made within the scope of the present invention as defined by the appended claims.

The invention claimed is:

1. A medical image processing method of determining a fractional flow reserve through a stenosis of a coronary artery from medical image data, the medical image data comprising a set of images of a coronary region of a patient, the coronary region comprising the stenosis, the method comprising:
    reconstructing a three dimensional model of a coronary artery tree of the patient from the medical image data;
    determining stenosis dimensions from the three dimensional model of the coronary artery tree of the patient;
    simulating blood flow in the three dimensional model of the coronary artery tree of the patient to determine modeled flow rates;
    using an analytical model depending on the stenosis dimensions to predict a modeled pressure drop over the stenosis from the modeled flow rates by determining a radius of inviscid core depending on a stenosis length and a flow rate and comparing the radius of inviscid core with a threshold to determine whether to include an entrance effect in the analytical model; and
    determining the fractional flow reserve through the stenosis from the modeled pressure drop.

2. The method according to claim 1, wherein simulating blood flow in the three dimensional model of the coronary artery tree of the patient to determine modeled flow rates comprises simulating steady state blood flow.

3. The method according to claim 2, wherein simulating steady state blood flow comprises iteratively determining steady state fluid resistance and pressure values.

4. The method according to claim 3, wherein iteratively determining steady state fluid resistance and pressure values comprises iteratively updating the steady state fluid resistance and pressure values with an under-relaxation scheme.

5. The method according to claim 3, wherein the three dimensional model of the coronary artery tree of the patient comprises at least one inlet and a plurality of outlets, the method further comprising estimating a total inlet flow into the three dimensional model of the coronary artery tree of the patient from the medical image data and wherein iteratively determining steady state fluid resistance and pressure values comprises iteratively updating the steady state fluid resistance and pressure values until a total outlet flow from the plurality of outlets matches the total inlet flow.

6. The method according to claim 1, wherein simulating blood flow in the three dimensional model of the coronary artery tree of the patient to determine modeled flow rates comprises simulating hyperemic blood flow.

7. The method according to claim 1, wherein the analytical model is based upon a modified version of the Bernoulli equation.

8. A method of assessing the functional significance of coronary artery stenosis from medical image data, the method comprising:
determining a fractional flow reserve through a stenosis of a coronary artery from the medical image data according to the method of claim 1; and
comparing the fractional flow reserve through the stenosis of the coronary artery with a threshold to assess the functional significance of the coronary artery stenosis.

9. The method according to claim 8, wherein comparing the fractional flow reserve through the stenosis of the coronary artery with a threshold to assess the functional significance of the coronary artery stenosis comprises classifying the stenosis as an ischemic lesion if the fractional flow reserve through the stenosis of the coronary artery is less than the threshold.

10. The method according to claim 8, wherein comparing the fractional flow reserve through the stenosis of the coronary artery with a threshold to assess the functional significance of the coronary artery stenosis comprises classifying the stenosis as a non-ischemic lesion if the fractional flow reserve through the stenosis of the coronary artery is greater than the threshold.

11. The method according to claim 8, wherein the threshold is 0.8.

12. The computer readable medium carrying processor executable instructions which when executed on a processor cause the processor to carry out a method according to claim 1.

13. A medical image processing system for determining a fractional flow reserve through a stenosis of a coronary artery from medical image data, the medical image data comprising a set of images of a coronary region of a patient, the coronary region comprising the stenosis, the system comprising:
a computer processor and a data storage device, the data storage device having a three dimensional model reconstruction module; a stenosis dimension determination module; a blood flow simulation module; an analytical modeling module; and a fractional flow reserve determination module comprising non-transitory instructions operative by the processor to:
reconstruct a three dimensional model of a coronary artery tree of the patient from the medical image data;
determine stenosis dimensions from the three dimensional model of the coronary artery tree of the patient;
simulate blood flow in the three dimensional model of the coronary artery tree of the patient to determine modeled flow rates;
use an analytical model depending on the stenosis dimensions to predict a modeled pressure drop over the stenosis from the modeled flow rates by determining a radius of inviscid core depending on a stenosis length and a flow rate and comparing the radius of inviscid core with a threshold to determine whether to include an entrance effect in the analytical model; and
determine the fractional flow reserve through the stenosis from the modeled pressure drop.

14. The system according to claim 13, wherein the blood flow simulation module comprises non-transitory instructions operative by the processor to: simulate blood flow in the three dimensional model of the coronary artery tree of the patient to determine modeled flow rates by simulating steady state blood flow.

15. The system according to claim 14, wherein the blood flow simulation module comprises non-transitory instructions operative by the processor to: simulate steady state blood flow by iteratively determining steady state fluid resistance and pressure values.

16. The system according to claim 15, wherein the blood flow simulation module comprises non-transitory instructions operative by the processor to: iteratively determining steady state fluid resistance and pressure values by iteratively updating the steady state fluid resistance and pressure values with an under-relaxation scheme.

17. The system according to claim 15, wherein the blood flow simulation module comprises non-transitory instructions operative by the processor to: estimate a total inlet flow into the three dimensional model of the coronary artery tree of the patient from the medical image data and wherein iteratively determining steady state fluid resistance and pressure values comprises iteratively updating the steady state fluid resistance and pressure values until a total outlet flow from all outlets of the three dimensional model of the coronary artery tree of the patient matches the total inlet flow.

18. The system according to claim 13, wherein the blood flow simulation module comprises non-transitory instructions operative by the processor to: simulate blood flow in the three dimensional model of the coronary artery tree of the patient to determine modeled flow rates by simulating hyperemic blood flow.

19. The system according to claim 13, wherein the analytical model is based upon a modified version of the Bernoulli equation.

20. The system according to claim 13, the data storage device further comprising a threshold comparison module comprising non-transitory instructions operative by the processor to:
compare the fractional flow reserve through the stenosis of the coronary artery with a threshold to assess the functional significance of the coronary artery stenosis.

21. The system according to claim 13, wherein the threshold comparison module further comprises non-transitory instructions operative by the processor to: classify the stenosis as an ischemic lesion if the fractional flow reserve through the stenosis of the coronary artery is less than the threshold.

22. The system according to claim 13, wherein the threshold comparison module further comprises non-transitory instructions operative by the processor to: classify the stenosis as a non-ischemic lesion if the fractional flow reserve through the stenosis of the coronary artery is greater than the threshold.

23. The system according to claim 13, wherein the threshold is 0.8.

* * * * *